United States Patent
Sugimoto et al.

(10) Patent No.: US 8,817,263 B2
(45) Date of Patent: *Aug. 26, 2014

(54) SAMPLE ANALYSIS ELEMENT AND DETECTING DEVICE

(71) Applicant: Seiko Epson Corporation, Tokyo (JP)

(72) Inventors: Mamoru Sugimoto, Chino (JP); Jun Amako, Tsurugashima (JP); Hideaki Koike, Chino (JP)

(73) Assignee: Seiko Epson Corporation (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/743,822

(22) Filed: Jan. 17, 2013

(65) Prior Publication Data

US 2013/0182257 A1    Jul. 18, 2013

(30) Foreign Application Priority Data

Jan. 18, 2012   (JP) ................................. 2012-008161

(51) Int. Cl.
*G01N 21/55*   (2014.01)
(52) U.S. Cl.
CPC .............. *G01N 21/55* (2013.01); *G01N 21/554* (2013.01)
USPC ........................................................ 356/445
(58) Field of Classification Search
CPC .............................. G01N 21/55; G01N 21/554
USPC ................. 356/445, 301, 317–318; 422/68.1, 422/82.05, 82.09; 436/171, 164, 524
See application file for complete search history.

(56) References Cited

U.S. PATENT DOCUMENTS

| 7,079,250 | B2 | 7/2006 | Mukai |
| 7,088,449 | B1 * | 8/2006 | Brongersma ................. 356/445 |
| 7,351,588 | B2 | 4/2008 | Poponin |
| 7,399,445 | B2 | 7/2008 | Kuroda et al. |
| 7,483,130 | B2 * | 1/2009 | Baumberg et al. ............ 356/301 |
| 7,639,355 | B2 | 12/2009 | Fattal et al. |
| 7,733,491 | B2 | 6/2010 | Kuroda et al. |

(Continued)

FOREIGN PATENT DOCUMENTS

| EP | 2 372 348 | 10/2011 |
| JP | 2000-356587 | 12/2000 |

(Continued)

OTHER PUBLICATIONS

Jean Cesario, "Electromagnetic Coupling Between a Metal Nanoparticle Grating and a Metallic Surface", Optical Society of America, Optics Letters, vol. 30, No. 24, Dec. 15, 2005, pp. 3404-3406.

(Continued)

*Primary Examiner* — Sang Nguyen
(74) *Attorney, Agent, or Firm* — Harness, Dickey & Pierce, P.L.C.

(57) ABSTRACT

A plurality of metallic nano-body groups that includes metallic nano-bodies which are dispersed on a dielectric surface at a first pitch smaller than the wavelength of incident light is arranged in one direction at a second pitch that resonates with the incident light. Localized surface plasmon resonance occurs in the metallic nano-body by the action of the incident light. Propagating surface plasmon resonance occurs by the action of the second pitch. The propagating surface plasmon resonance is combined with the localized surface plasmon resonance. A so-called hybrid mode is established.

10 Claims, 14 Drawing Sheets

(56) References Cited

U.S. PATENT DOCUMENTS

| | | | |
|---|---|---|---|
| 7,768,640 B2 * | 8/2010 | Cunningham et al. | 356/317 |
| 8,085,405 B2 | 12/2011 | Ogawa | |
| 8,093,065 B2 | 1/2012 | Poponin | |
| 8,107,071 B2 * | 1/2012 | Kimura | 356/318 |
| 8,247,216 B2 | 8/2012 | Zaccarin et al. | |
| 2006/0194344 A1 | 8/2006 | Saito | |
| 2008/0198376 A1 | 8/2008 | Poponin | |
| 2009/0109422 A1 * | 4/2009 | Handa et al. | 356/39 |
| 2010/0167946 A1 * | 7/2010 | Shaw et al. | 506/9 |
| 2010/0178713 A1 | 7/2010 | Nishiuma et al. | |
| 2011/0114859 A1 | 5/2011 | Amako et al. | |
| 2011/0116088 A1 | 5/2011 | Amako et al. | |
| 2012/0019828 A1 * | 1/2012 | McCaffrey et al. | 356/432 |
| 2012/0107958 A1 | 5/2012 | Poponin | |
| 2012/0257204 A1 * | 10/2012 | Walters | 356/445 |

FOREIGN PATENT DOCUMENTS

| | | |
|---|---|---|
| JP | 2003-268592 | 9/2003 |
| JP | 2003-270132 | 9/2003 |
| JP | 2006-208057 | 8/2006 |
| JP | 2007-218900 | 8/2007 |
| JP | 2007-240361 | 9/2007 |
| JP | 2007-248284 | 9/2007 |
| JP | 2007-303973 | 11/2007 |
| JP | 2008-292425 | 12/2008 |
| JP | 2009-222401 | 10/2009 |
| JP | 2011-128133 | 6/2011 |
| JP | 2011-128135 | 6/2011 |
| JP | 2011-141264 | 7/2011 |
| JP | 2011-141265 | 7/2011 |

OTHER PUBLICATIONS

N. Felidj et al., "Enhanced Substrate-Induced Coupling in Two-Dimensional Gold Nanoparticle Arrays", Physical Review B 66, The American Physical Society, 2002, pp. 245407-1 through 245407-7.

Y. Chu et al., "Experimental Study of the Interaction Between Localized and Propagating Surface Plasmons", Optical Society of America, Optics Letters, vol. 34, No. 3, Feb. 1, 2009, pp. 244-246.

L. Du et al., "Localized Surface Plasmons, Surface Plasmon Polaritons, and Their Coupling in 2D Metallic Array for SERS", Optical Society of America, Optics Express, vol. 18, No. 3, Feb. 1, 2010, pp. 1959-1965.

M. Inoue et al., "Surface Enhanced Raman Scattering by Metal Spheres, I. Cluster Effect", Journal of the Physical Society of Japan, vol. 52, No. 11, Nov. 1983, pp. 3853-3864.

* cited by examiner

SAMPLE ANALYSIS ELEMENT AND DETECTING DEVICE

BACKGROUND

1. Technical Field

The present invention relates to a sample analysis element, a detecting device, and the like that are provided with a metallic nano-body such as a metallic nanoparticle or a metallic nano-projection.

2. Related Art

A sample analysis element using localized surface plasmon resonance (LSPR) is known. Such a sample analysis element is provided with metallic nano-bodies, that is, metallic nanoparticles which are dispersed on, for example, a dielectric surface. The metallic nanoparticle is formed sufficiently smaller than the wavelength of excitation light, for example. If the metallic nanoparticle is irradiated with the excitation light, all electric dipoles are aligned, and thus an enhanced electric field is induced. As a result, near-field light is generated on the surface of the metallic nanoparticle. A so-called hot spot is formed.

In Yizhuo Chu et al, "Experimental study of the interaction between localized and propagating surface plasmons", OPTICS LETTERS, U.S.A. Feb. 1, 2009, Vol. 34, No. 3, p. 244-246, the metallic nanoparticles are disposed in a lattice form at a predetermined pitch. If the size of the pitch is set to be a specific numerical value, propagating surface plasmon resonance (PSPR) based on an evanescent wave occurs. The propagating surface plasmon resonance is combined with the localized surface plasmon resonance. A so-called hybrid mode is established. In this way, the localized surface plasmon resonance is enhanced by the propagating surface plasmon resonance, and thus the near-field light is intensified on the surface of the metallic nanoparticle.

The sample analysis element described above can be used in a target substance detection device. As disclosed in Yizhuo Chu et al, "Experimental study of the interaction between localized and propagating surface plasmons", OPTICS LETTERS, U.S.A. Feb. 1, 2009, Vol. 34, No. 3, p. 244-246, if the pitch is set to be the wavelength of the evanescent wave that causes the propagating surface plasmon resonance, the surface density of the hot spot is significantly reduced on the dielectric surface, and thus the target substance cannot be easily stuck to the hot spot.

SUMMARY

An advantage of some aspects of the invention is that a sample analysis element and a detecting device can be provided in which it is possible to combine propagating surface plasmon resonance with localized surface plasmon resonance while increasing the surface density of a hot spot.

(1) An aspect of the invention is directed to a sample analysis element including: a substrate, a metal film is formed on the surface of the substrate, a dielectric film is formed on the surface of the metal film, a plurality of metallic nano-body groups that includes metallic nano-bodies which are dispersed on the dielectric surface at a first pitch smaller than the wavelength of incident light and that is arranged in one direction at a second pitch which resonates with the incident light.

Localized surface plasmon resonance occurs in the metallic nano-body by the action of the incident light. Propagating surface plasmon resonance based on an evanescent wave occurs by the action of the pitch (the second pitch) of the metallic nano-body group. The propagating surface plasmon resonance is combined with the localized surface plasmon resonance. A so-called hybrid mode is established. In this way, the localized surface plasmon resonance is enhanced by the propagating surface plasmon resonance, and thus, near-field light is intensified on the surface of the metallic nano-body. A so-called hot spot is formed. In addition, since a plurality of metallic nano-bodies is disposed in each metallic nano-body group, compared to a case where metallic nano-body simple bodies are disposed at a pitch that resonates with incident light, the surface density of the metallic nano-body is increased. Therefore, the surface density of the hot spot is increased.

(2) In the sample analysis element according to the above aspect, a region that does not include the metallic nano-body may be formed between the metallic nano-body groups. That is, in a space that is divided by a pair of mutually parallel imaginary planes which sandwiches the metallic nano-body groups therebetween, a gap between adjacent metallic nano-body groups is filled with an insulator (including a space). In other words, in the space, a metal material is excluded from the space between adjacent metallic nano-body groups.

(3) In the sample analysis element according to the above aspect, when the metallic nano-bodies are dispersed in one direction at the first pitch smaller than the second pitch in the metallic nano-body group, the gap between the metallic nano-body groups may be set to be larger than the first pitch of an array of the metallic nano-bodies. As such, according to the setting of the distance, the propagating surface plasmon resonance can reliably occur.

(4) In the sample analysis element according to the above aspect, the second pitch may be set to be a certain size to establish a primary minimum value of reflectance at a wavelength shorter than the resonance wavelength of the localized surface plasmon resonance that is generated in the metallic nano-body and to establish the minimum value of a higher order than a primary order. If the second pitch is set in this manner, reflectance is significantly reduced at a specific wavelength. As a result, propagating surface plasmon is reliably combined with localized surface plasmon. The near-field light is reliably intensified on the surface of the metallic nano-body.

(5) In the sample analysis element according to the above aspect, the second pitch may be set to be a certain size to establish the minimum value of reflectance at a wavelength that is red-shifted from the resonance wavelength of the localized surface plasmon resonance that is generated in the metallic nano-body. As such, according to the setting of the second pitch, reflectance is further reduced. The near-field light can be enhanced as expected.

(6) In the sample analysis element according to the above aspect, the metallic nano-body groups may be arranged at the second pitch in one direction and also arranged at the second pitch in a direction intersecting the one direction. In such a sample analysis element, the pitches can be set in two directions intersecting each other. As a result, the propagating surface plasmon resonance can be established in two directions. As a result, incident light can have a plurality of polarization planes. The incident light can have circularly-polarized light.

(7) In the sample analysis element according to the above aspect, a region that does not include the metallic nano-body may be formed between the subdivided metallic nano-body groups. That is, in a space that is divided by a pair of mutually parallel imaginary planes which sandwiches the metallic nano-body groups therebetween, a gap between adjacent metallic nano-body groups is filled with an insulator (including a space). In other words, in the space, a metal material is excluded from the space between adjacent metallic nano-body groups.

(8) The sample analysis element as described above can be used in a detecting device. The detecting device may include, for example, a light source that emits light toward the metallic nano-body group of the sample analysis element, and a photodetector that detects the light that is emitted from the metallic nano-body group according to the irradiation of the light.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, an embodiment of the invention will be described with reference to the accompanying drawings. In addition, the embodiment that is described below does not unduly limit the contents of the invention stated in the appended claims, and all of the configurations that are described in this embodiment are not necessarily essential as solving means of the invention.

1. Structure of Sample Analysis Element

Figure 1:
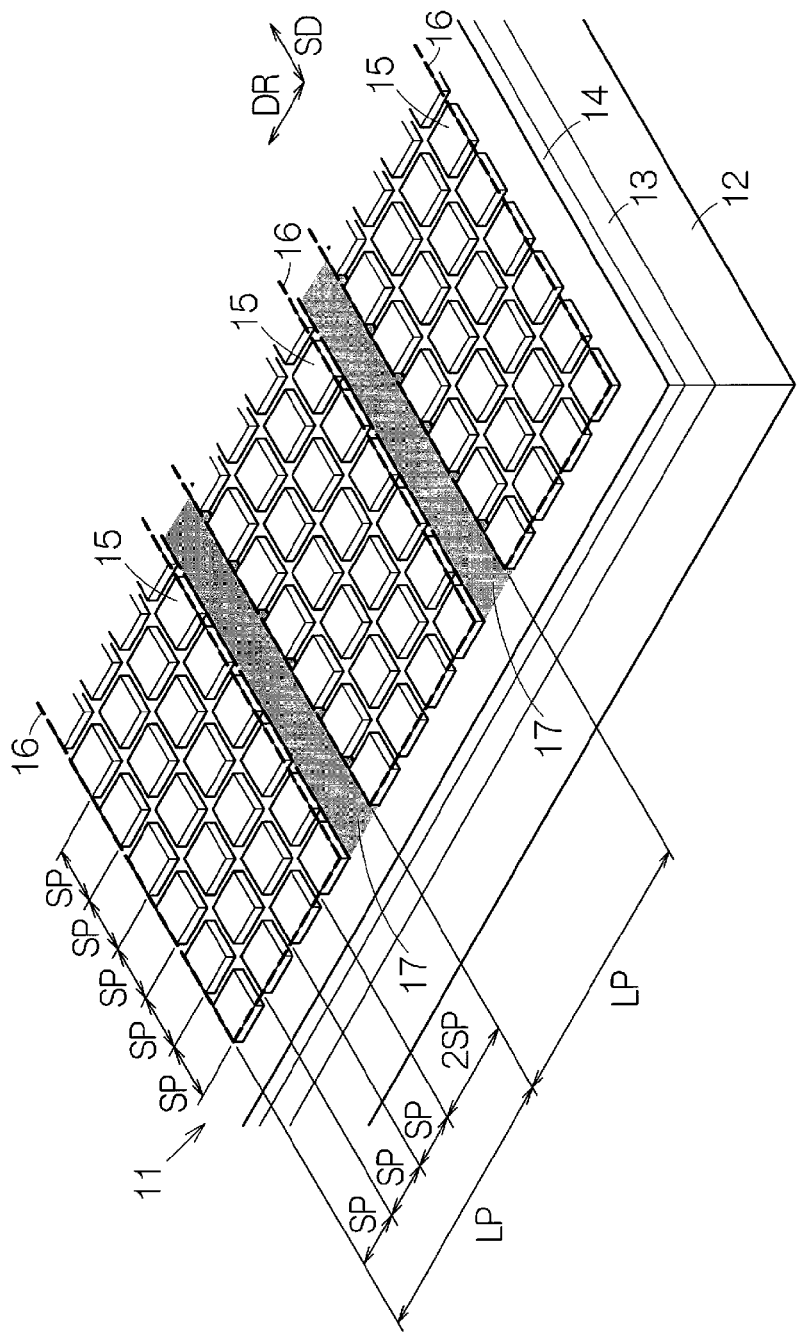
FIG. 1 is a perspective view schematically showing a sample analysis element according to an embodiment of the invention.

FIG. 1 schematically shows a sample analysis element 11 according to an embodiment of the invention. The sample analysis element 11 includes a substrate 12. The substrate 12 is formed of, for example, a dielectric. As for the type of dielectric, for example, glass can be used.

A metal film 13 is formed on the surface of the substrate 12. The metal film 13 is formed of metal. The metal film 13 can be formed of, for example, gold. The metal film 13 can be formed, for example, on the surface of the substrate 12 in a continuous way over the entire surface. The film thickness of the metal film 13 can be set to be greater than or equal to about 100 nm, for example.

A dielectric film (a dielectric) 14 is formed on the surface of the metal film 13. The dielectric film 14 is formed of a dielectric. The dielectric film 14 can be formed of an oxide film such as $SiO_2$, for example. The dielectric film 14 can be formed, for example, on the surface of the metal film 13 in a continuous way over the entire surface. The film thickness of the dielectric film 14 can be set to be about 40 nm, for example.

A metallic nano-projection (a metallic nano-body) 15 is formed on the surface of the dielectric film 14. The metallic nano-projections 15 are dispersed on the surface of the dielectric film 14. The metallic nano-projection 15 is formed of metal. The metallic nano-projection 15 can be formed of, for example, silver. In addition, gold or aluminum may also be used to form the metallic nano-projection 15. Each metallic nano-projection 15 is formed in a rectangular column. The horizontal cross-section of the rectangular column is formed in, for example, a square. The length of one side of the square can be set to be in a range of 1 nm to 1000 nm, for example. The height (from the surface of the dielectric film) of the rectangular column can be set to be in a range of 10 nm to 100 nm, for example. The horizontal cross-section of the rectangular column may also be formed in a polygonal shape other than a square. The metallic nano-projection 15 may also be formed in a circular column or other three-dimensional shapes.

The metallic nano-projections 15 form a metallic nano-projection group (a metallic nano-body group) 16. The metallic nano-projection groups 16 are arranged at a predetermined long pitch LP (a second pitch) in a first direction (one direction) DR. The size of the long pitch LP is set according to the wavenumber of an evanescent wave, as will be described later. A non-metallic region that does not include the metallic nano-projection (a region that does not include the metallic nano-projection) 17 is formed between the metallic nano-projection groups 16. That is, in a space that is sandwiched between an imaginary plane that includes the bottom surfaces of the metallic nano-projections 15 and an imaginary plane that includes the top surfaces of the metallic nano-projections 15, a gap between adjacent metallic nano-projection groups 16 is filled with an insulator (including a space). In other words, in the space, a metal material is excluded from the space between adjacent metallic nano-projection groups 16. Here, the surface of the dielectric film 14 is exposed between the metallic nano-projection groups 16.

The metallic nano-projections 15 are disposed at a short pitch SP (a first pitch) in the first direction DR in each metallic nano-projection group 16. At the same time, the metallic nano-projections 15 are disposed at the short pitch SP (the first pitch) in a second direction SD intersecting the first direction DR in each metallic nano-projection group 16. Here, the second direction SD is perpendicular to the first direction DR in one imaginary plane that includes the surface of the dielectric film 14. Therefore, a plurality of metallic nano-projections 15 is disposed in a lattice form at the short pitch SP in each metallic nano-projection group 16. The short pitch SP is set to be smaller than at least the long pitch LP. In the metallic nano-projection group 16, the gap between adjacent metallic nano-projections 15 is set to be smaller than the gap between adjacent metallic nano-projection groups 16, that is, the width of the non-metallic region 17 that is specified in the first direction DR. Here, the width of the non-metallic region 17 is set to be larger than the short pitch SP. That is, the gap between the metallic nano-projection groups 16 is set to be larger than the short pitch SP.

Figure 2:
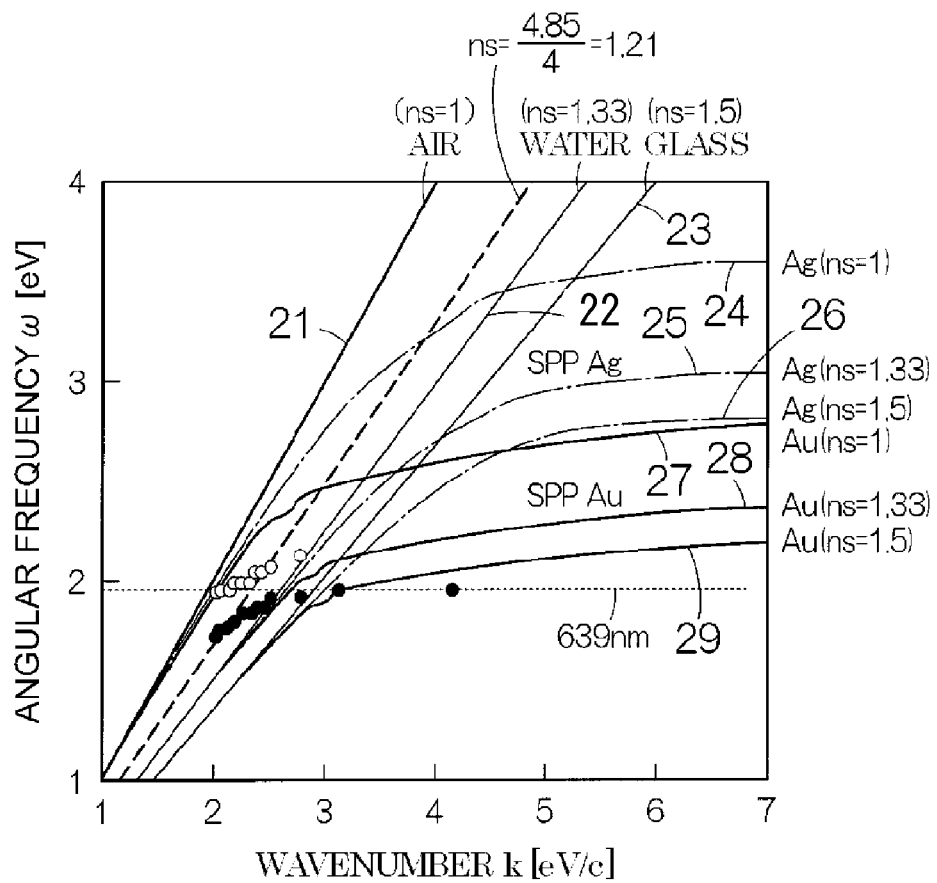
FIG. 2 is a graph showing dispersion relation.

FIG. 2 shows dispersion relation. A wavenumber k is specified according to the long pitch LP. Straight lines 21, 22, and 23, respectively, show the dispersion relations of air (ns=1.0), water (ns=1.33), and glass (ns=1.5). These dispersion relations show a proportional relation. Three curved lines 24, 25, and 26 show the dispersion relations of the propagating surface plasmon resonance of silver Ag for each refractive index (ns=1.0, 1.33, and 1.5). In addition, three curved lines 27, 28, and 29 show the dispersion relations of the propagating surface plasmon resonance of gold Au for each refractive index (ns=1.0, 1.33, and 1.5). A straight line parallel to an x axis (a wavenumber) shows the angular frequency (=1.94 eV) (wavelength=639 nm) of the localized surface plasmon resonance of the metallic nano-projection 15. A white plot shows the angular frequency of incident light that forms a primary peak (an extreme value) of electric field intensity at the metallic nano-projection 15 for each long pitch LP. A black plot shows the angular frequency of incident light that forms a secondary peak of electric field intensity at the metallic nano-projection 15 for each long pitch LP. The long pitch LP is set to be a certain length that is specified at a wavenumber which shows the peak of electric field intensity at incident light having an angular frequency deviated from the angular frequency of localized surface plasmon resonance.

In the sample analysis element 11, the size of each metallic nano-projection 15 is set to be sufficiently smaller than the wavelength of incident light. As a result, in the metallic nano-projection 15, the localized surface plasmon resonance (LSPR) occurs by the action of incident light. In addition, if the planarization plane of incident light is fitted to an x-axis direction, the propagating surface plasmon resonance (PSPR) based on an evanescent wave occurs according to the setting of the long pitch LP. The propagating surface plasmon resonance is combined with the localized surface plasmon resonance of the metallic nano-projection 15. A so-called hybrid mode is established. In this way, the localized surface plasmon resonance is enhanced by the propagating surface plasmon resonance, and thus, near-field light is intensified on the surface of the metallic nano-projection 15. A so-called hot spot is formed. In addition, since in each metallic nano-projection group 16, the gap between the metallic nano-projections 15 is set to be the short pitch SP smaller than the long pitch LP, compared to a case where the gap between the metallic nano-projections 15 is set to be the long pitch LP, the surface density of the metallic nano-projection 15 is increased. The surface density of the hot spot is increased.

In the sample analysis element 11, the long pitch LP is set to be a certain size to establish a primary minimum value of reflectance at a wavelength shorter than the resonance wavelength of the localized surface plasmon resonance that is generated in the metallic nano-projection 15 and to establish the minimum value of a higher order than a primary order at the value of reflectance smaller than the primary minimum value of reflectance. If the long pitch LP is set in this manner, reflectance is significantly reduced at a specific wavelength. As a result, propagating surface plasmon is reliably combined with localized surface plasmon. The near-field light is reliably intensified on the surface of the metallic nano-projection 15. In particular, it is preferable that the long pitch LP be set to be a certain size to establish the minimum value of reflectance at a wavelength that is red-shifted from the resonance wavelength of the localized surface plasmon resonance that is generated in the metallic nano-projection 15. As such, according to the setting of the long pitch LP, reflectance can show "0" (zero). The near-field light can be enhanced as expected.

2. Verification of Electric Field Intensity

Figure 3A:
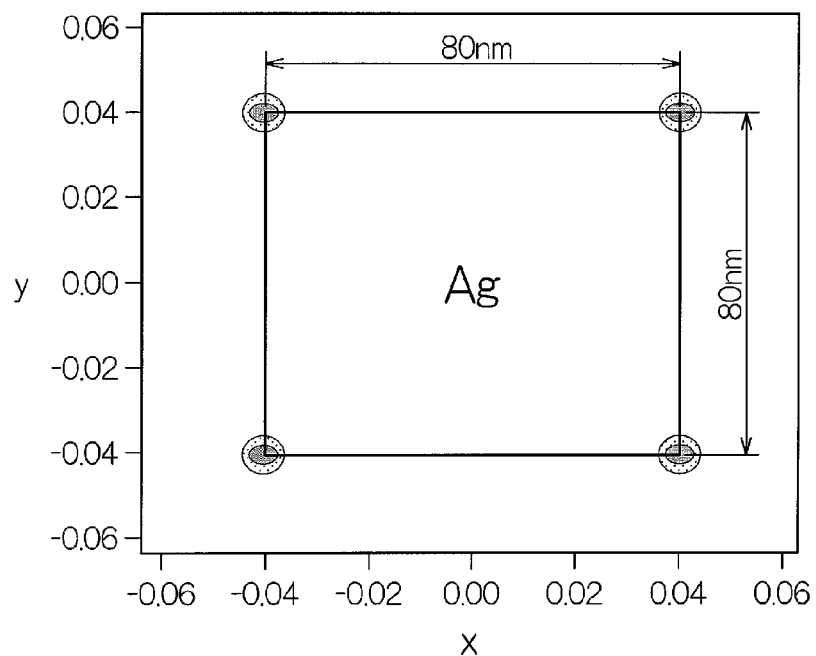
FIGS. 3A and 3B, respectively, are a plan view and a side view showing a unitary unit of a simulation model.
Figure 3B:
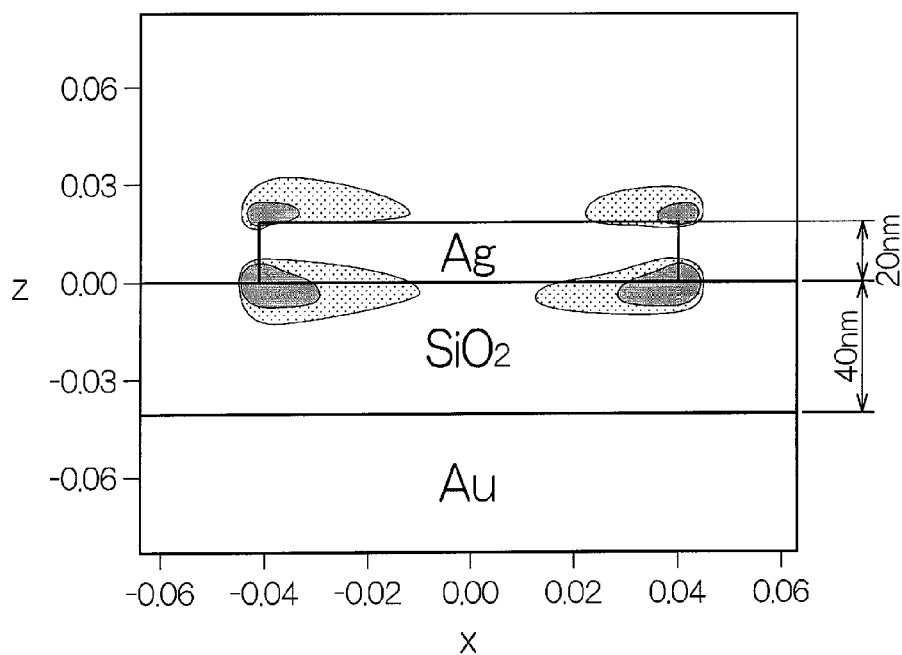

The inventor verified the electric field intensity of the sample analysis element 11. In the verification, simulation software of a FDTD (Finite-Difference Time-Domain) method was used. As shown in FIGS. 3A and 3B, the inventor constructed a unitary unit of a simulation model on the basis of a Yee Cell. In the unitary unit, the dielectric film 14 made of $SiO_2$ was formed on the metal film 13 made of gold and having a size of 120 nm square. The film thickness of the dielectric film 14 was set to be 40 nm. The metallic nano-projection 15 made of silver and having a size of 80 nm square was formed on the dielectric film 14. The height (from the surface of the dielectric film) of the metallic nano-projection 15 was set to be 20 nm.

Figure 4A:
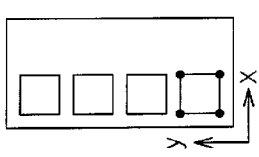
FIGS. 4A to 4G, respectively, are plan views of a first model, a second model, a third model, a fourth model, a fifth model, a sixth model, and a first comparative model of the simulation model.
Figure 4B:
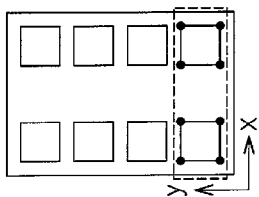
Figure 4C:
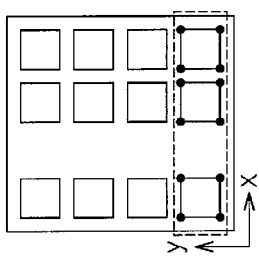
Figure 4D:
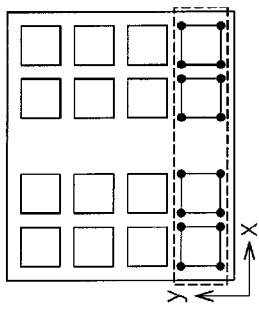
Figure 4E:
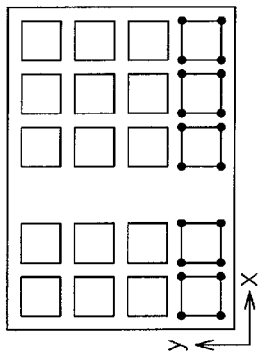
Figure 4F:
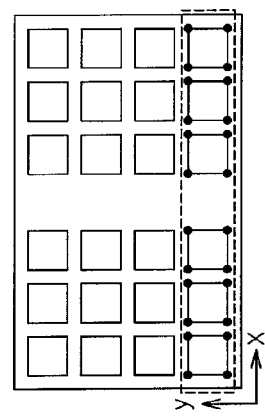

As shown in FIG. 4A, in a first model, the long pitch LP of the metallic nano-projection group 16 in the x-axis direction was set to be 240 nm. A single metallic nano-projection group 16 was constituted by a row of unitary units, that is, metallic nano-projections 15. As a result, the non-metallic region 17 was formed between the metallic nano-projection groups 16 by a row of void unitary units. The void unitary unit was constituted by a void having a size of 120 nm square. Electric field intensity Ex was calculated at the leading metallic nano-projection 15. A peripheral refractive index ns was set to 1. Incident light that is linearly-polarized light was set. A polarization plane was fitted to the x-axis direction. The incident light was set to be vertically incident. In the metallic nano-projection 15, electric fields were concentrated on four vertices on the upper side and four vertices on the lower side.

As shown in FIGS. 4B to 4F, in a second model to a sixth model, the long pitches LP of the metallic nano-projection groups 16 in the x-axis direction were set, respectively, to be 360 nm, 480 nm, 600 nm, 720 nm, and 840 nm. In each model, a single metallic nano-projection group 16 was constituted by each of; two rows, three rows, four rows, five rows, and six rows of unitary units, that is, metallic nano-projections 15. As a result, the non-metallic region 17 was formed by a row of void unitary units between the metallic nano-projection groups 16 for each model. The void unitary unit was constituted by a void having a size of 120 nm square. Similarly to the first model, the electric field intensity Ex was calculated at the leading metallic nano-projection 15 for each model.

Figure 4G:
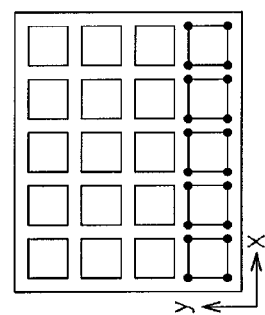
Figure 5:
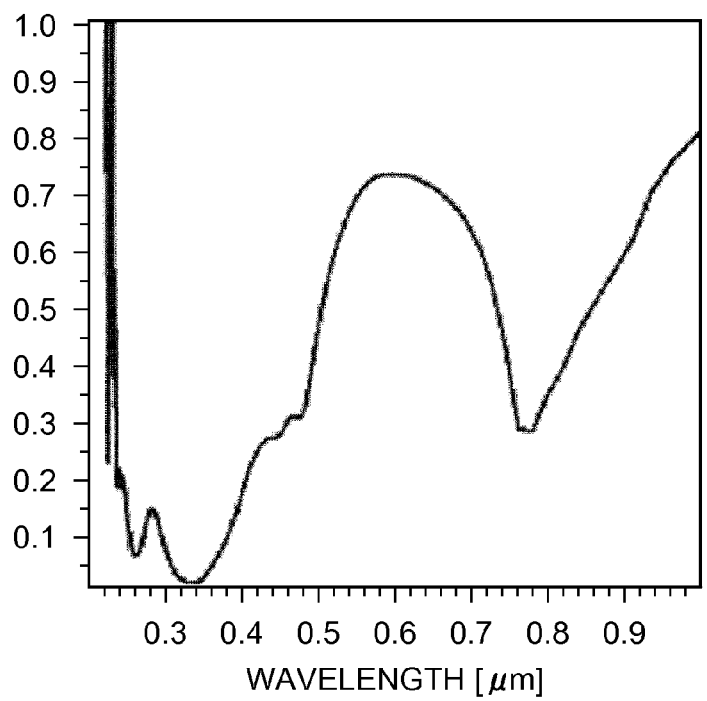
FIG. 5 is a graph showing the wavelength dependence of reflectance of the first comparative model.

As shown in FIG. 4G, the inventor prepared a first comparative model. In the first comparative model, the non-metallic region 17 was omitted. That is, the metallic nano-projection group 16 was not set. The metallic nano-projections 15 were simply disposed in a lattice form at the short pitch SP. In the same manner as described above, the electric field intensity Ex was calculated at the selected single metallic nano-projection 15.

Figure 6:
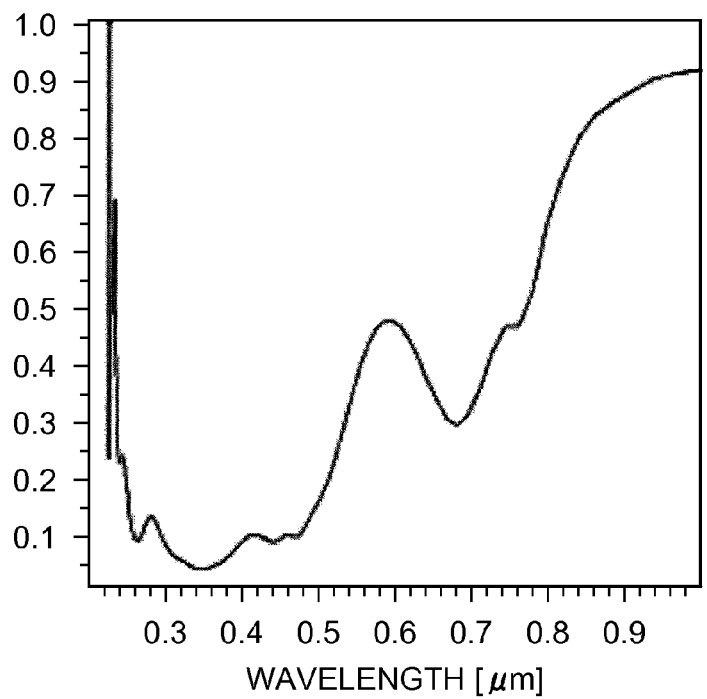
FIG. 6 is a graph showing the wavelength dependence of reflectance of the first model.
Figure 7:
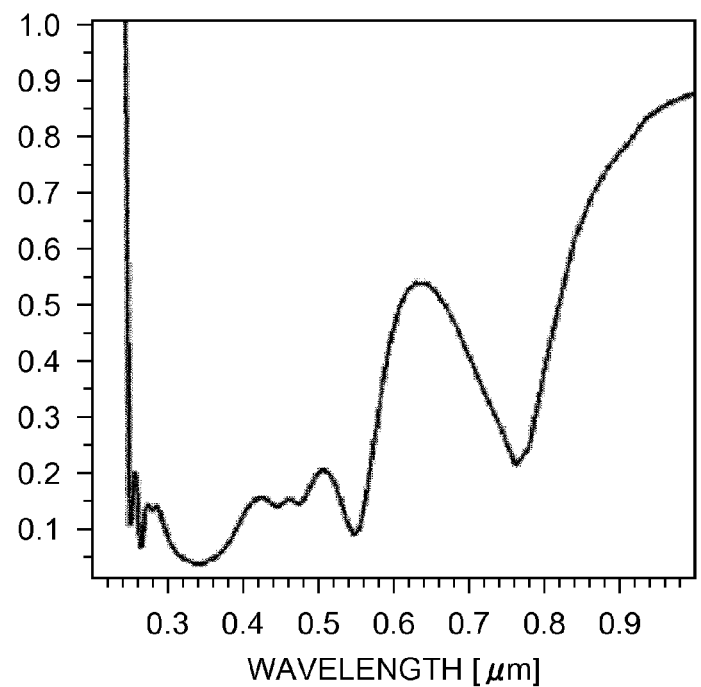
FIG. 7 is a graph showing the wavelength dependence of reflectance of the second model.
Figure 8:
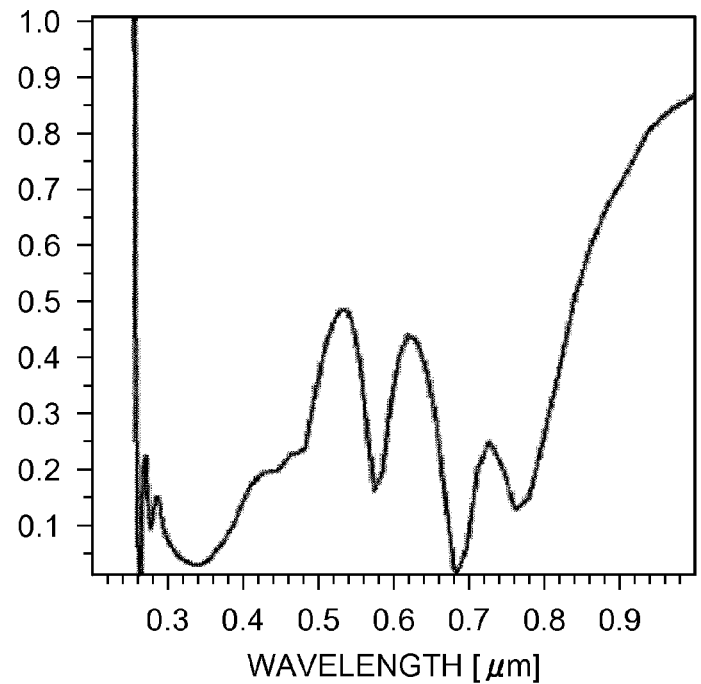
FIG. 8 is a graph showing the wavelength dependence of reflectance of the third model.
Figure 9:
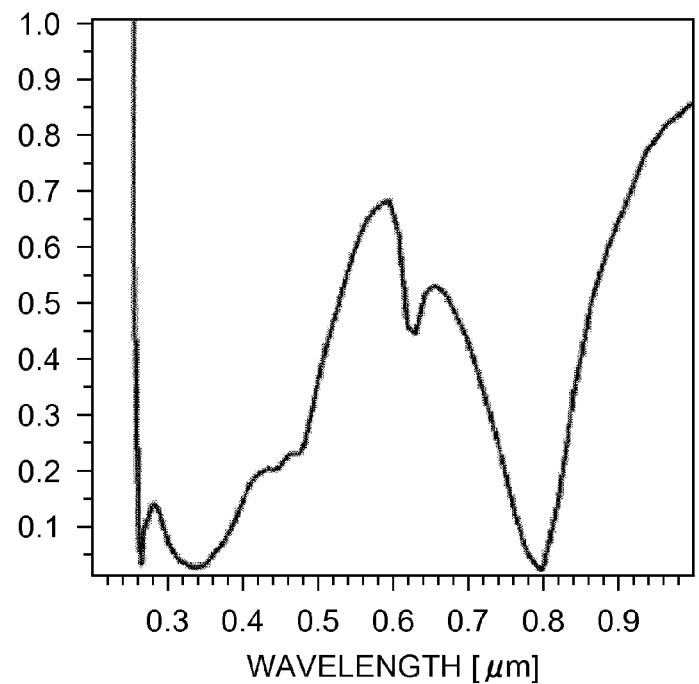
FIG. 9 is a graph showing the wavelength dependence of reflectance of the fourth model.
Figure 10:
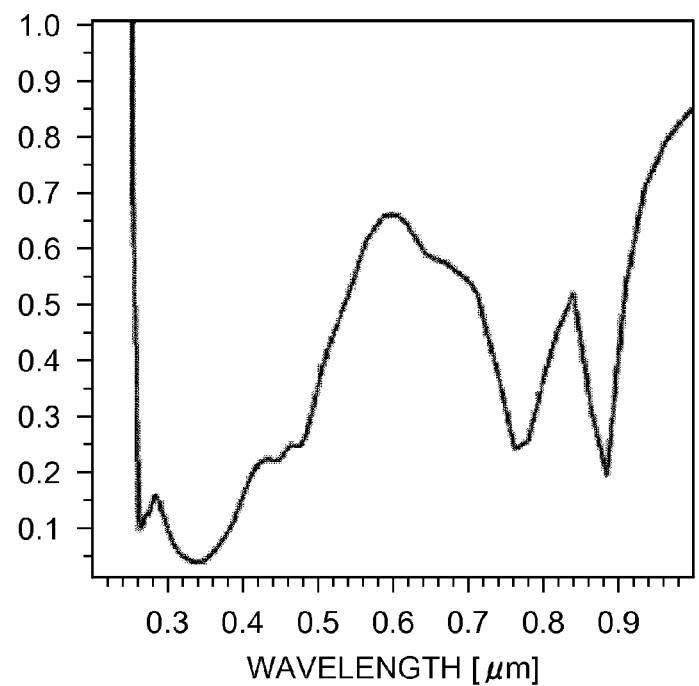
FIG. 10 is a graph showing the wavelength dependence of reflectance of the fifth model.
Figure 11:
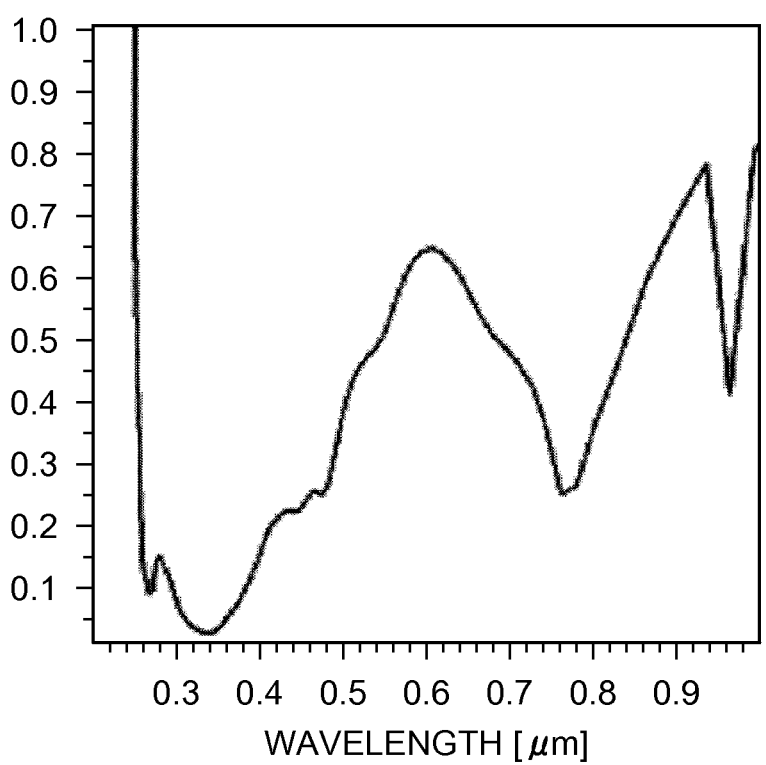
FIG. 11 is a graph showing the wavelength dependence of reflectance of the sixth model.

FIGS. 5 to 11 show the wavelength dependence of reflectance of each model. If the local electric field resonance occurs, a decrease in reflectance is observed. As shown in FIGS. 6 and 7, in the first model and the second model, a secondary minimum value was observed in the vicinity of a wavelength of 770 nm. As shown in FIG. 8, in the third model, a tertiary minimum value was observed at 770 nm. In this manner, in the vicinity of the wavelength of 770 nm, if the pitch widens in states such as the first model, the second model, and the third model, reflectance gradually decreases, and as shown in FIG. 9, in the fourth model, reflectance showed substantially "0" (zero) at the wavelength of 800 nm. In addition, as shown in FIGS. 10 and 11, in the fifth model and the sixth model, the primary minimum value was observed at the wavelength of 770 nm. If the pitch widens in states such as the fifth model and the sixth model, reflectance at the wavelength of 770 nm increased. Further, as is apparent from FIG. 8, in the third model, reflectance became "0" (zero) at the wavelength of 685 nm.

Figure 12:
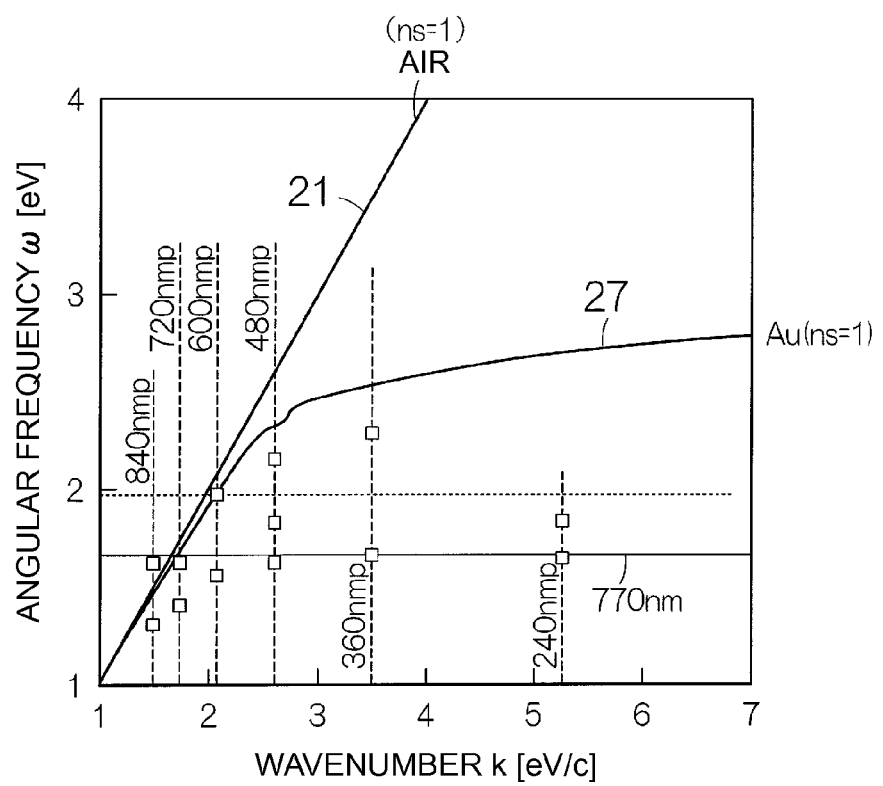
FIG. 12 is a graph showing dispersion relation prepared based on the minimum value of the reflectance in FIGS. 6 to 11.

FIG. 12 shows dispersion relation prepared from the minimum value of the reflectance of each model. A frequency (a vertical axis) showing the minimum value of reflectance was plotted for each wavenumber (a horizontal axis) resulting from the long pitch LP. At the minimum value (equivalent to the primary minimum value) showing a high frequency for each long pitch LP, the direction of a dipole is the same direction in gold (Au) and silver (Ag), and at the minimum value (equivalent to the minimum value of a high order higher than a primary order) showing a low frequency for each long pitch LP, the directions of dipoles of gold (Au) and silver (Ag) are the opposite directions. A wavelength (=770 nm) appearing in common to a plurality of long pitches LP in FIG. 12 is equivalent to the resonance wavelength of the localized surface plasmon resonance. This is because the inclination of dispersion relation shows the moving speed of propagation plasmon, the inclination of an angular frequency showing the minimum value of a high order in each of; the first model (LP=240 nm), the second model (LP=360 nm), and the third model (LP=480 nm) shows "0" (zero), and similarly, the inclination of an angular frequency showing the primary minimum value in the fifth model (LP=720 nm) and the sixth model (LP=840 nm) shows "0" (zero). The resonance wavelength of the localized surface plasmon resonance can be determined depending on the volume of the metallic nano-projection 15 or the film thickness of the dielectric film 14. Further, a wavelength showing the minimum value of reflectance outside the resonance wavelength (=770 nm) of the localized surface plasmon for each long pitch LP is mainly considered as propagating surface plasmon. In addition, in the second model (LP=360 nm) and the third model (LP=480 nm), it is observed that the angular frequency of the minimum value of a high order is shifted from a dispersion relation curve of Au (ns=1) to the low frequency side. This is due to the row of the metallic nano-projections 15. It is the result that as the row of the metallic nano-projections increases, interaction between the metallic nano-projections 15 increases, and thus a resonance wavelength is red-shifted, that is, shifted to the long wavelength side. A longer wavelength or red-shift of a resonance peak wavelength shows the intensity of interaction between the metallic nano-projection 15 groups. Anti-Crossing Behavior (known as an indicator of a hybrid mode) was observed, similarly to Yizhuo Chu et al, "Experimental study of the interaction between localized and propagating surface plasmons", OPTICS LETTERS, U.S.A. Feb. 1, 2009, Vol. 34, No. 3, p. 244-246, based on a dispersion relation curve of the wavelength of 770 nm and the propagating surface plasmon resonance of gold Au (ns=1). In addition, since the secondary minimum value (wavelength: 685 nm) of the third model is established by a wavelength almost corresponding with the primary minimum value (wavelength: 682 nm) of the first model, it is understood that the secondary minimum value of the third model derives from the localized surface plasmon resonance that occurs in the non-metallic region 17 that does not include the metallic nano-projection 15.

Figure 13:
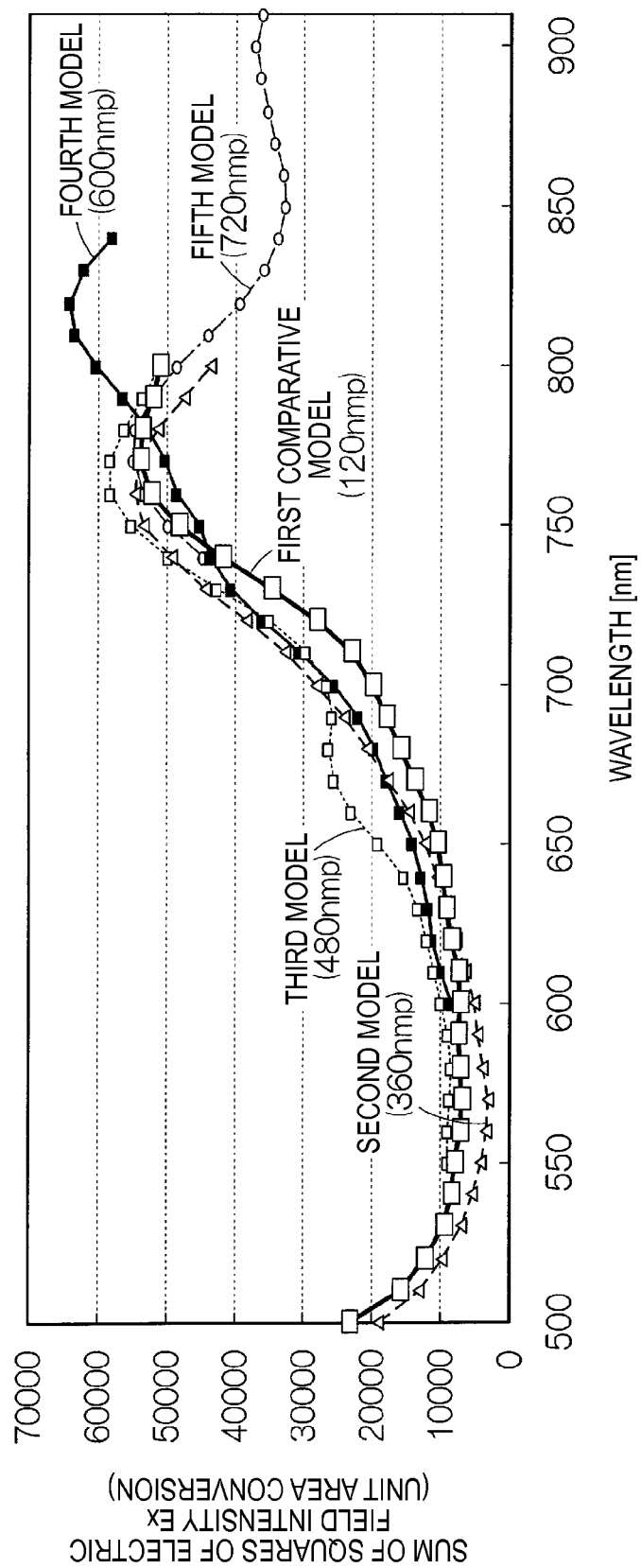
FIG. 13 is a graph showing the wavelength dependence of the sum of squares of electric field intensity converted to unit area calculated at a vertex on the lower side of a metallic nano-projection for each model of the second to the fifth models and the first comparative model.

FIG. 13 shows the wavelength dependence of the electric field intensity Ex in the same way. Here, the sum of squares of the electric field intensity Ex converted per unit area was specified. In the specification of the sum of squares, the electric field intensity Ex was calculated at each of four vertices on the lower side of the metallic nano-projection 15. The square value of the electric field intensity Ex was calculated for each vertex and the square values of all the vertices of the minimum unit of repeated calculation were summed. The area of the first comparative model was set as a unit area. The summed result was converted per unit area. In this way, the sum of squares of the electric field intensity Ex per unit area was calculated. As is apparent from FIG. 13, it was confirmed that the electric field intensity Ex of the metallic nano-projection 15 was increased in all of the metallic nano-projections 15 according to the setting of the long pitch LP. In particular, since in the first comparative model, a peak value appears at the wavelength of 770 nm due to the influence of the short pitch SP, it is considered that the localized surface plasmon resonance is dominant due to the influence of the short pitch SP in the second to the fifth models. In addition, in the third model in which the long pitch LP is 480 nm, compared to the first comparative model, significant improvement in the electric field intensity Ex was observed at the wavelengths of 680 nm and 770 nm. In the fourth model in which the long pitch LP is 600 nm, significant improvement in the electric field intensity Ex exceeding the square value of the electric field intensity Ex of the localized surface plasmon resonance of the wavelength of 770 nm was observed at the wavelengths of 820 nm. It is considered that the localized surface plasmon of the wavelength of 770 nm causes strong interaction with the propagating surface plasmon of the metallic nano-projection 15 and as a result, a resonance wavelength is red-shifted to the wavelength of 820 nm. From the above, it can be found that in the model having this configuration, the long pitch LP is set to be in a range of 480 nm to 600 nm, whereby very large electric field enhancement is obtained. This can also be read from the dispersion relation in FIG. 12. That is, it can be found that the long pitch LP beginning to red-shift from the resonance wavelength 770 nm of the localized surface plasmon resonance in a hybrid mode is in a range of 480 nm to 600 nm.

Figure 14A:
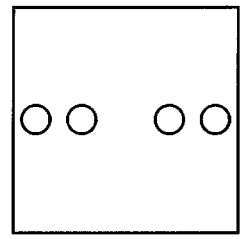
FIGS. 14A to 14D are plan views of a seventh model, an eighth model, a ninth model, and tenth model of the simulation model.
Figure 14B:
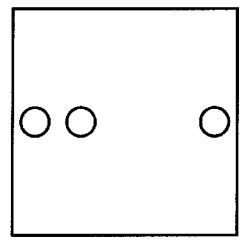
Figure 14C:
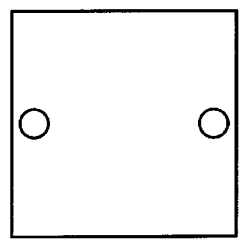
Figure 14D:
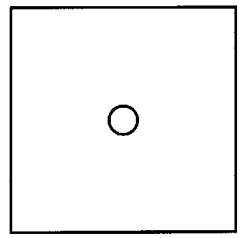

In addition, the inventor constructed a circular columnar unitary unit in place of the rectangular columnar unitary unit. The diameter of a circular cross-section was set to be 80 nm. The height (from the surface of the dielectric film) was set to be 20 nm. In any model, the long pitch LP of the metallic nano-projection group 16 in the x-axis direction was fixed at 600 nm. As shown in FIG. 14A, in a seventh model, a single metallic nano-projection group 16 was constituted by four rows of unitary units, that is, metallic nano-projections 15. The non-metallic region 17 was formed by a row of void unitary units between the metallic nano-projection groups 16. As shown in FIGS. 14B to 14D, in an eighth model to a tenth model, a single metallic nano-projection group 16 was constituted by each of; three rows, two rows, and a row of unitary units, that is, metallic nano-projections 15. Therefore, in the eighth to the tenth models, the non-metallic region 17 was formed by each of; two rows, three rows, and four rows of void unitary units between the metallic nano-projection groups 16. In the metallic nano-projection 15, electric field intensity Ez was calculated at a lower end of a cylindrical surface coming into contact with an x-z plane. At the same time, the inventor prepared a second comparative model. In the second comparative model, the rectangular columnar metallic nano-projection 15 of the first comparative model was changed to a circular column. In the second comparative model, the non-metallic region 17 was omitted, similarly to the first comparative model.

Figure 15:
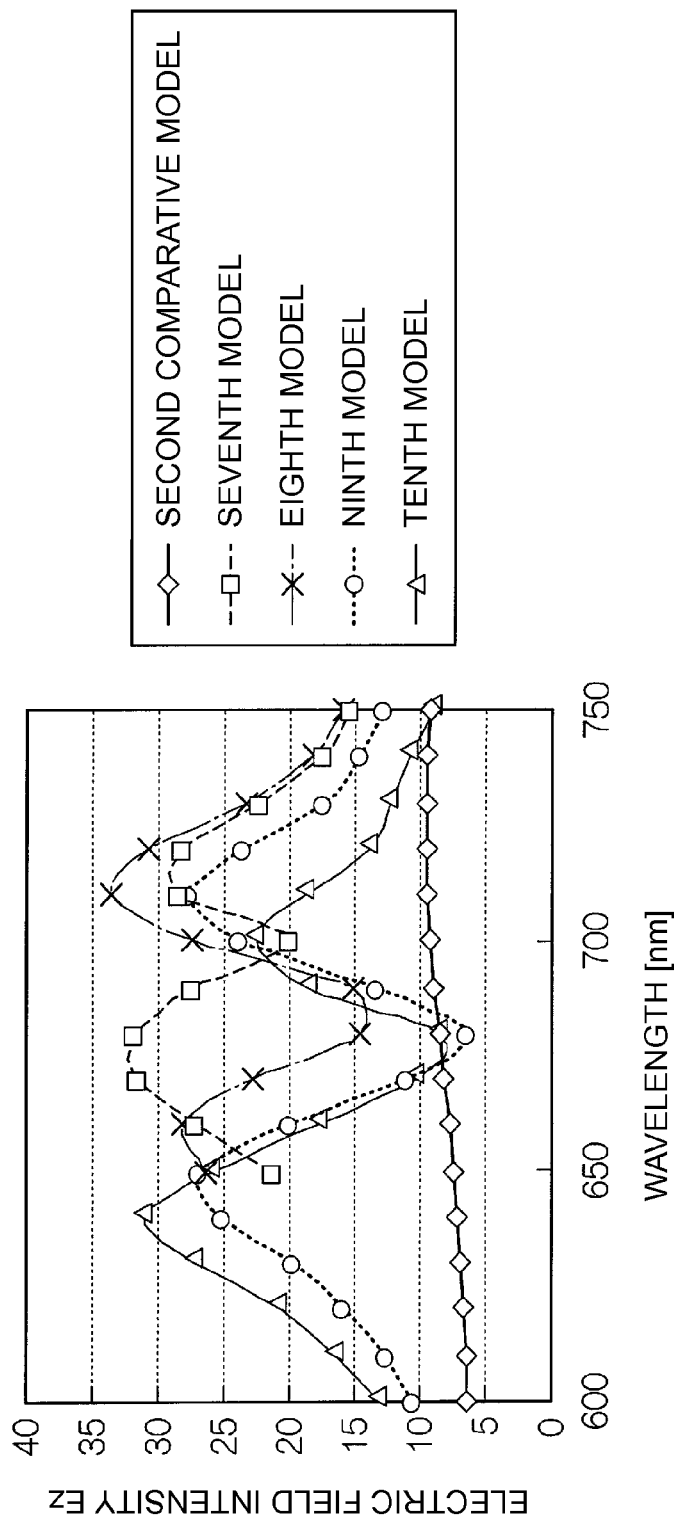
FIG. 15 is a graph showing the wavelength dependence of electric field intensity calculated at one point on the lower side of a metallic nano-projection for each model of the seventh to the tenth models and the second comparative model.

As is apparent from FIG. 15, it was confirmed that the electric field intensity Ez of the metallic nano-projection 15 was increased according to the setting of the long pitch LP (=600 nm). In addition, it was observed that the peak values of the electric field intensity Ez were almost the same regardless of the size of the gap between the metallic nano-projection groups 16, that is, the width of the non-metallic region 17. In addition, it was observed that if the width of the non-metallic region 17 increases, the frequency of the peak value is shifted to the high frequency side, that is, the low wavelength side. In addition, as described above, in the second to the fifth models and the first comparative model, the electric field intensity Ex was calculated in the x-axis direction. On the other hand, in the seventh to the tenth models and the second comparative model, the electric field intensity Ez was calculated in the z-axis direction. Such a difference is due to a difference in a placing method of the Yee Cell of FDTD calculation, and in all of these, the effect of an enhanced electric field is captured in the same way.

3. Method of Manufacturing Sample Analysis Element

The sample analysis element 11 can be manufactured by a known manufacturing method. That is, the substrate 12 is prepared in the manufacturing of the sample analysis element 11. The metal film 13 and the dielectric film 14 are laminated in order, on the surface of the substrate 12. It the lamination, for example, a plating method or a sputtering method may be used. On the surface of the insulating film 14, a laminated film is formed on one surface by a material of the metallic nano-projection 15. On the surface of the laminated film, a mask modeled the metallic nano-projection 15 is formed. In the mask, for example, a resist film may be used. If the laminated film is removed around the mask, each metallic nano-projection 15 is shaped from the laminated film. As such, shaping, etching treatment or milling treatment may be carried out.

4. Detecting Device

Figure 16:
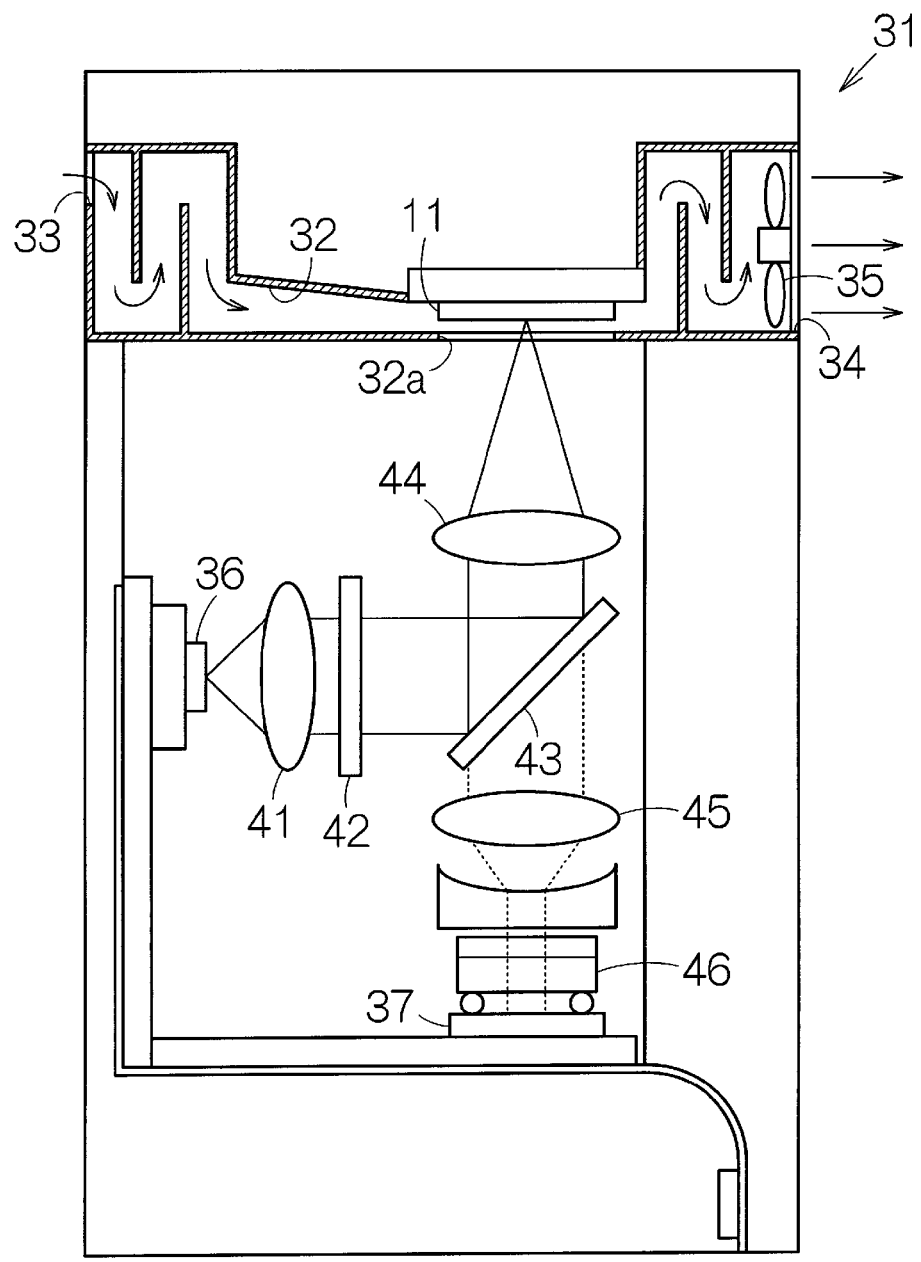
FIG. 16 is a schematic diagram schematically showing a detecting device according to an embodiment of the invention.

FIG. 16 schematically shows a detecting device 31 according to an embodiment of the invention. The detecting device 31 uses surface-enhanced Raman scattering (SERS). The detecting device 31 can detect target substances such as an adenovirus, a rhinovirus, a HIV virus, or an influenza virus, for example, on the basis of the surface-enhanced Raman scattering. The sample analysis element 11 described above, that is, a sensor chip is incorporated into the detecting device 31. In the incorporation, a transport path 32 is partitioned in the detecting device 31. A carrying-in port 33 and a discharge port 34 are formed in the transport path 32. The transport path 32 is hermetically sealed between the carrying-in port 33 and the discharge port 34. A blower fan 35 is installed in the transport path 32. The blower fan 35 generates an air current toward the discharge port 34 from the carrying-in port 33. A sample (=a mass of air) is entrained by the air current, thereby moving in the transport path 32 from the carrying-in port 33 to the discharge port 34. The sample analysis element 11 described above is installed in the transport path 32.

A light source 36 is incorporated into the detecting device 31. As the light source 36, for example, a laser light source that emits laser light can be used. The light source 36 emits light, for example, at a specific wavelength.

A photodetector 37 is incorporated into the detecting device 31. As the photodetector 37, for example, a light-receiving element can be used. The light-receiving element can detect, for example, the intensity of light. The light-receiving element can output a detection current according to, for example, the intensity of light. Therefore, the intensity of light can be specified according to the magnitude of an electric current that is output from the light-receiving element.

An optical system is constructed between the light source 36 and the sample analysis element 11 and between the sample analysis element 11 and the photodetector 37. The optical system 38 forms an optical path between the light source 36 and the sample analysis element 11, and at the same time, forms an optical path between the sample analysis element 11 and the photodetector 37. The light of the light source 36 is led to the sample analysis element 11 by the action of the optical system 38. The reflected light of the sample analysis element 11 is led to the photodetector 37 by the action of the optical system.

The optical system includes a collimator lens 41, a polarization control element 42, a dichroic mirror 43, an objective lens 44, a condensing lens 45, and an etalon 46. The dichroic mirror 43 is disposed, for example, between the sample analysis element 11 and the photodetector 37. The objective lens 44 is disposed between the dichroic mirror 43 and the sample analysis element 11. Light passes through a transmission window 32a of the transport path 32 between the sample analysis element 11 and the objective lens 44. The transmission window 32a is blocked by, for example, a transmission material. The transmission material allows the transmission of the light from the light source 36. The condensing lens 45 and the etalon 46 are disposed between the dichroic mirror 43 and the photodetector 37. The optical axes of the objective lens 44 and the condensing lens 45 are fitted coaxially. The optical axis of the light source 36 is perpendicular to the optical axes of the objective lens 44 and the condensing lens 45. The surface of the dichroic mirror 43 intersects these optical axes at an angle of 45 degrees. The collimator lens 41 and the polarization control element 42 are disposed between the dichroic mirror 43 and the light source 36. In this way, the collimator lens 41 faces the light source 36. The optical axis of the collimator lens 41 is coaxially fitted to the optical axis of the light source 36.

The light that is emitted from the light source 36 is converted into parallel light by the collimator lens 41. The polarization control element 42 converts the light into linearly-polarized light. The linearly-polarized light is reflected by the dichroic mirror 43. The reflected light is condensed by the objective lens 44 and irradiated to the sample analysis element 11. At this time, the light can be incident in a vertical direction perpendicular to the surface of the substrate 12. A so-called vertical incidence can be established. The polarization plane of the light is fitted to the x-axis direction of the sample analysis element 11. The localized surface plasmon resonance occurs in the metallic nano-projection 15 by the action of the light irradiated. At the same time, the propagating surface plasmon resonance based on the evanescent wave occurs. The propagating surface plasmon resonance is combined with the localized surface plasmon resonance (LSPR) of the metallic nano-projection 15. Near-field light is intensified on the surface of the metallic nano-projection 15. A so-called hot spot is formed.

At this time, if the target substance is stuck to the metallic nano-projection 15 by the hot spot, Rayleigh-scattering light and Raman scattering light are generated from the target substance. A so-called surface-enhanced Raman scattering is achieved. As a result, the light is emitted toward the objective lens 44 in a spectrum according to the type of the target substance.

The light that is emitted from the sample analysis element 11 in this manner is converted into parallel light by the objective lens 44 and passes through the dichroic mirror 43. Thereafter, the light is condensed by the condensing lens 45. The condensed light is incident on the etalon 46. The etalon 46 disperses the Raman scattering light. In this way, the photodetector 37 detects the intensity of the light for each specific wavelength. As a result, the target substance can be detected according to the spectrum of the light. It is favorable if the spectrum of the target substance is measured in advance and stored in the detecting device 31. The detected spectrum is compared with the spectrum measured in advance.

5. Modification Example of Sample Analysis Element

Figure 17:
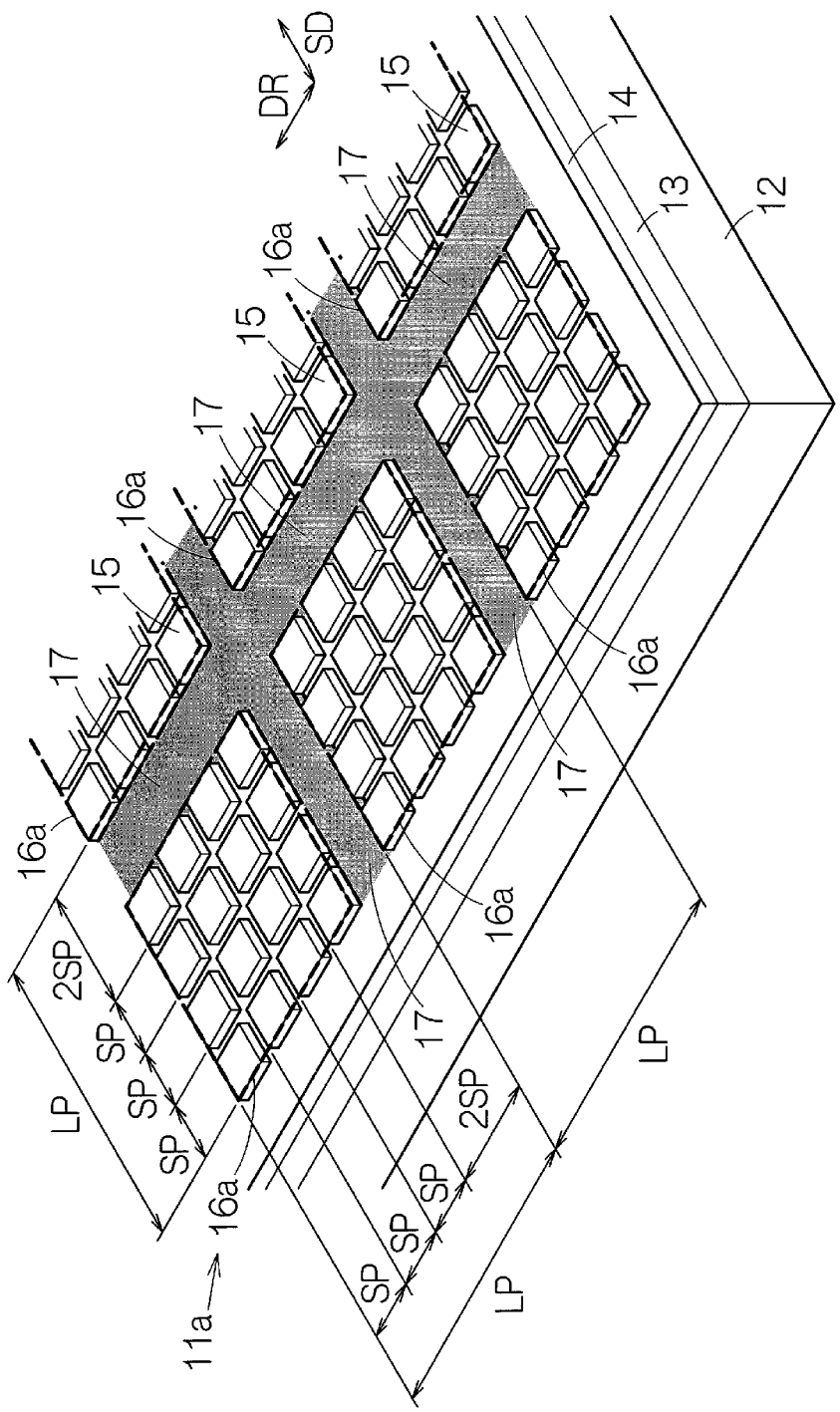
FIG. 17 is a perspective view schematically showing a sample analysis element according to a modification example.

FIG. 17 schematically shows a sample analysis element 11a according to a modification example. In the sample analysis element 11a, a metallic nano-projection group 16a is subdivided in the second direction SD as well as the first direction DR described above. That is, the metallic nano-projection groups 16a are arranged at the predetermined long pitch LP in the first direction DR and at the same time, arranged at the predetermined long pitch LP in the second direction SD. In this way, the non-metallic regions that do not include the metallic nano-projection (the regions that do not include the metallic nano-projection) 17 are formed between the metallic nano-projection groups 16a in the second direction SD as well as the first direction DR. In addition, the configuration of the sample analysis element 11a according to the modification example is the same as that of the sample analysis element 11 described above. In the drawing, a configuration or a structure equivalent to that in the sample analysis element 11 described above is denoted by the same reference numeral and description thereof is omitted.

In the sample analysis element 11a, if incident light that is circularly-polarized light is irradiated, the propagating surface plasmon resonance based on the evanescent wave occurs according to the setting of the long pitch LP in the x-axis direction and the y-axis direction. The propagating surface plasmon resonance is combined with the localized surface plasmon resonance of the metallic nano-projection 15. A so-called hybrid mode is established. In this way, the localized surface plasmon resonance is enhanced by the propagating surface plasmon resonance, and thus the near-field light is intensified on the surface of the metallic nano-projection 15. A so-called hot spot is formed. In addition, since in each metallic nano-projection group 16a, the gap between the metallic nano-projections 15 is set to be the short pitch SP smaller than the long pitch LP, compared to a case where the gap between the metallic nano-projections 15 is set to be the long pitch LP, the surface density of the metallic nano-projection 15 is increased. The surface density of the hot spot is increased. In addition, in a case where the sample analysis element 11a is incorporated into the detecting device 31, it is favorable if the light source 36 emits light that is circularly-polarized light.

In addition, in a single metallic nano-projection group 16, so-called island-shaped metallic nano-projections 15 may also be disposed in a random manner. In such a case, the metallic nano-projection group 16 can be divided by geometric contour lines such as straight line or curved lines. The non-metallic region 17 can be established between the contour lines of the metallic nano-projection groups 16. It is favorable if the non-metallic region 17 extends, for example, in a uniform width. The island-shaped metallic nano-projection 15 can be formed based on aggregation of metal materials in thin-film formation by sputtering.

In addition, this embodiment has been described in detail, as described above. However, it will be easily understood by those skilled in the art that many modifications are possible which do not substantively depart from the new matters and the advantageous effects of the invention. Therefore, all of such modification examples are included in the scope of the invention. For example, the term stated at least once along with a different term in a broader sense or the same meaning in the specification or the drawings can be replaced with a different term in any place of the specification or the drawings. Further, the configurations and the operations of the sample analysis element, the detecting device, and the like are also not limited to those described in the embodiment and various modifications are possible.

The entire disclosure of Japanese Patent Application No. 2012-008161 filed Jan. 18, 2012 is expressly incorporated by reference herein.

What is claimed is:

1. A sample analysis element comprising:
a substrate;
a metal film is formed on the surface of the substrate;
a dielectric film is formed on the surface of the metal film; and
plurality of metallic nano-body groups that includes metallic nano-bodies which are dispersed at a first pitch smaller than the wavelength of incident light and that is formed on the dielectric surface,
wherein the plurality of metallic nano-body groups is arranged in one direction at a second pitch that resonates with the incident light,
a region that does not include the metallic nano-body is formed between adjacent metallic nano-body groups,
the metallic nano-bodies are dispersed in one direction at the first pitch smaller than the second pitch in the metallic nano-body group, and
the gap between adjacent metallic nano-body groups is larger than the first pitch.

2. The sample analysis element according to claim 1, wherein the second pitch is set to be a certain size to obtain a primary minimum value of reflectance at a wavelength shorter than the resonance wavelength of localized surface plasmon resonance that is generated in the metallic nano-body and to obtain the minimum value of a high order.

3. The sample analysis element according to claim 1, wherein the second pitch is set to be a certain size to obtain the minimum value of reflectance at a wavelength that is red-shifted from the resonance wavelength of localized surface plasmon resonance that is generated in the metallic nano-body.

4. The sample analysis element according to claim 1, wherein the metallic nano-body groups are arranged at the second pitch in one direction and also arranged at the second pitch in a direction intersecting the one direction.

5. The sample analysis element according to claim 4, wherein a region that does not include the metallic nano-body is formed between adjacent metallic nano-body groups.

6. A detecting device comprising:
a sample analysis element in which a plurality of metallic nano-body groups is arranged;
a light source that emits light toward the metallic nano-body group; and
a photodetector that detects the light that is emitted from the metallic nano-body group according to the irradiation of the light,
wherein the plurality of metallic nano-body groups includes metallic nano-bodies that are dispersed on a dielectric surface at a first pitch smaller than the wavelength of incident light, and the plurality of metallic nano-body groups is arranged in one direction at a second pitch that resonates with the incident light,
a region that does not include the metallic nano-body is formed between adjacent metallic nano-body groups,
the metallic nano-bodies are dispersed in one direction at the first pitch smaller than the second pitch in the metallic nano-body group, and
the gap between adjacent metallic nano-body groups is larger than the first pitch.

7. The detecting device according to claim 6, wherein the second pitch is set to be a certain size to obtain a primary minimum value of reflectance at a wavelength shorter than the resonance wavelength of localized surface plasmon resonance that is generated in the metallic nano-body and to obtain the minimum value of a high order.

8. The detecting device according to claim 6, wherein the second pitch is set to be a certain size to obtain the minimum value of reflectance at a wavelength that is red-shifted from the resonance wavelength of localized surface plasmon resonance that is generated in the metallic nano-body.

9. The detecting device according to claim 6, wherein the metallic nano-body groups are arranged at the second pitch in one direction and also arranged at the second pitch in a direction intersecting the one direction.

10. The detecting device according to claim 9, wherein a region that does not include the metallic nano-body is formed between adjacent metallic nano-body groups.

* * * * *